Nov. 19, 1940. K. SAWADA Plant Pat. 431
CAMELLIA
Filed Feb. 26, 1940
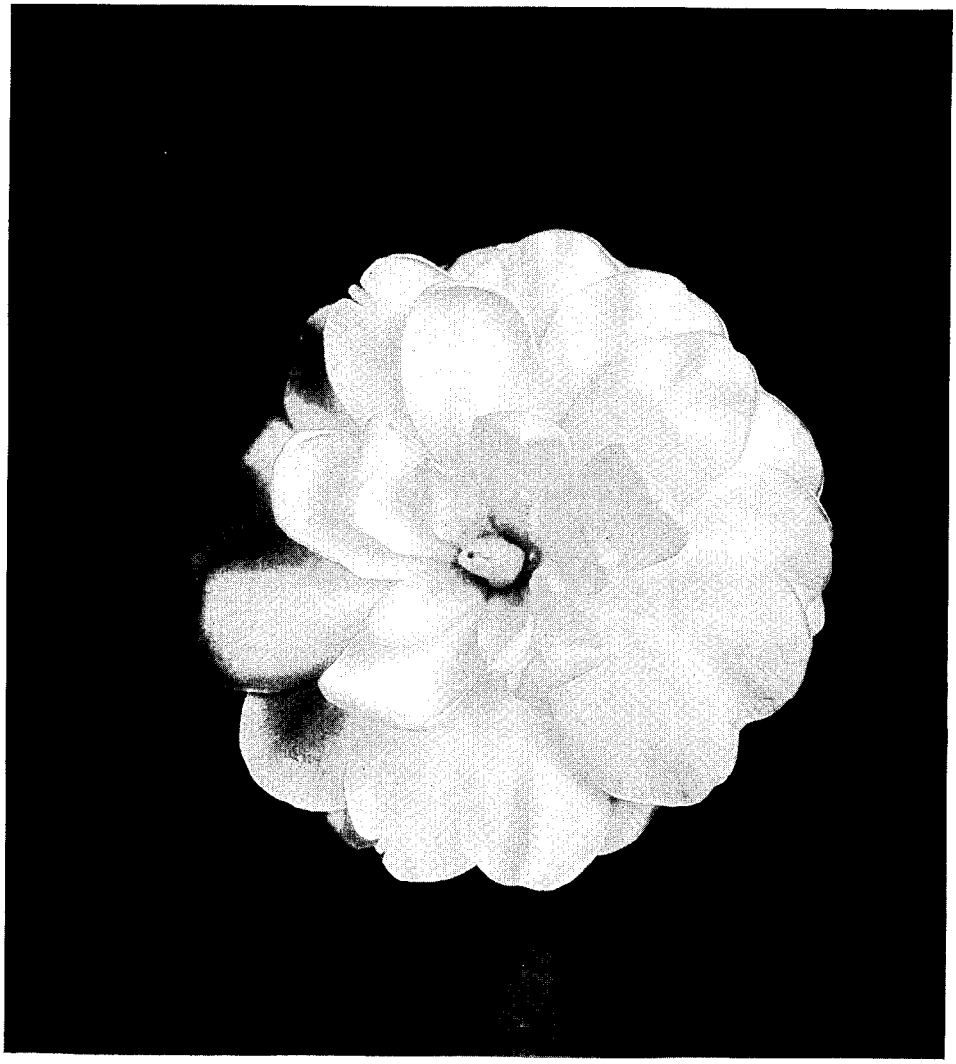
Inventor
Kosaku Sawada
By Rummler, Rummler & Davis
Attys Patented Nov. 19, 1940

Plant Pat. 431

UNITED STATES PATENT OFFICE

431

CAMELLIA

Kosaku Sawada, Crichton, Ala., assignor to Overlook Nurseries, Crichton, Ala., a partnership composed of Kosaku Sawada and S. Imura Application February 26, 1940, Serial No. 320,934

1 Claim. (Cl. 47—60)

The present discovery relates to a new and distinct variety of white camellia japonica and is the result of definite breeding efforts carried on since 1925. It is a seedling of "Sode-gakushi," the popular variety in Japan.

The improvement over other varieties pertains particularly to its vigorous growing habits, ease of propagation, abundance of size of blooms, keeping qualities, and resistance to disease and cold.

It is very difficult to obtain a full double flower from seeds; most of them are singles and semi-doubles. Although numerous plants were propagated during a period of fifteen years, only a few seedlings showed outstanding features. This new variety was grown in the field in the full sunlight, in a poor sandy soil. Some of the plants were grown under slats, and some in tubs in the greenhouse. Under these varying conditions, there has been no noticeable difference as to the color, shape, nor arrangement; but the number of blooms differed.

There are only about four named varieties of camellias. The "Alba Plena" perhaps so far is the most outstanding, but it is difficult to propagate and is easily injured by the cold. The "Candidissima" has a medium-sized flower, but is a slow and poor grower. "Purity" is a late flowering full double white, free flowering but also a slow grower. "Mathotiana Alba" is a good white but does not always develop perfect blooms. Many others which are listed as pure whites occasionally show a slight tint or streak of color.

The distinctive characteristics of this new camellia may be brought out more clearly by a comparison of the same with those of the white camellia "Alba Plena," the nearest named variety similar to it. The flower is slightly larger than the "Alba Plena" and does not flatten out like the latter. The petals are larger and roll or curve inward on the edges. The petals of the "Alba Plena" curve outward and downward. When fully open this improved camellia shows stamens, whereas the "Alba Plena" does not. Resistance to cold and diseases is much stronger in this improved variety and propagation by cuttings is more readily accomplished. The new camellia also grows faster than the "Alba Plena."

All of the above-mentioned characteristics of the blossom have been thoroughly established and remain true. Reproduction is asexual.

The superiority of this new variety over the "Alba Plena" was proved the winter of 1939–40, which was one of the severest in half a century for the part of Alabama where the plant was developed, the temperature going down to 10° above zero. Many of the "Alba Plena" plants were killed, while not a single plant of this new camellia was lost. The blooming period of the "Alba Plena" ended shortly by the freezing weather; but the new variety produced blooms after the weather moderated.

Sode-gakushi, the parent plant, has the following characteristics:

*Plant*

Type of growth: Loose, rather spreading.
Stems:
- *Color.*—Light brown.
- *Length.*—5 to 6 inches.
- *Branches.*—2 to 3 feet.
- *Thickness and strength.*—Rather slender but strong.

Leaves:
- *Size.*—Maximum length 3½ inches, maximum width 2 inches.
- *Color.*—Medium glossy green, sometimes variegated with yellow and white.

Sepals:
- *Number.*—4.
- *Length.*—½ to 1 inch.

*Flower*

Number of blossoms: 8 to 12 on one tree.
Color: Pure White.
Shape: Like a lotus bloom (nelumbium).
Size: 5½ to 6¾ inches across.
Number of petals: 3 rows, approximately 15.
Texture: Fine but firm.
Disease resistance: Good.
Lasting quality: Good.
Fragrance: Slight.

*Genital organs*

Stamens, anthers:
- *Size.*—Stamens, 1½ inches long.
- *Color.*—Anthers, yellow—stamens, white.
- *Number.*—Approximately 60 in a crown.
- *Arrangement.*—In form of a crown.

Pistils, styles:
- *Number.*—One.
- *Length.*—1½ inches.
- *Color.*—Greenish white.

Longevity (keeping qualities): Good.

The illustration shows a face view of the flower.

The following is a detailed description of this new variety:

*Plant*

Growth: Vigorous. Semi-upright, very compact and symmetrical. Ultimate height 15 to 20 feet.

*Blooming.*—December and January. Profuse and very free bloomer under all enviroments.

Stems:

*Color.*—Old wood is gray. New wood is brown.

*Length.*—6 to 8 inches and more.

*Branches.*—Very well branched.

*Thickness and strength.*—Medium.

*Glabrous.*

Leaves:

*Shape.*—Medium singly serrated, elliptic to lanceolate in shape.

*Size (average).*—Length 3 inches. Width 1½ inches.

*Evergreen.*

*Color.*—Glossy dark green.

*Texture.*—Leathery, medium thickness.

Sepals:

*Number.*—10 to 11.

*Length.*—¾ to 1 inch.

*Flower*

Arrangement: Fully imbricated. Very double.

Number of blossoms: One terminal flower; occasionally two on the terminus of the same stem.

How attached to peduncle: Firmly and directly.

Color: Uniform, pure white.

Shape: Ovate, slightly notched, involute.

Size: Generally from 4 to 5 inches in diameter; often much larger.

Number of petals: 50 to 70 with a few petalets.

Texture: Medium thickness.

Appearance: Porcelain-like, edge of petals roll inward.

Genital organs:

*Stamens.—Number*—20 to 30. *Length*—½ to ¾ inch.

*Color*—creamy white to yellow. *Arrangement*—in the center intermixed with about ten small petalets.

*Anthers.*—Yellow to brown color; very small.

*Pistils, styles.—Length*—½ to ¾ inch.

*Number*—pistil, 1. Style, 1. Stigma divided into 5 to 8 points. *Color*—creamy white.

*Ovaries.—Shape*—cylindrical.

*Number of cells*—generally 2, infrequently 1 or 3.

*Color*—brownish yellow.

*Disease resistance.*—Good; also resistant to freeze.

*Persistence.*—When the flower becomes old it drops; never hangs on and dries.

*Lasting quality.*—On the plant, about 2 weeks, in full bloom; as cut flower, several days and if in vase of water, one week.

*Fragrance.*—None.

The clear white color of this flower, together with its size, and, superior keeping qualities combine to provide a very desirable and exquisite product. Color terminology is in accordance with the ordinary dictionary definitions.

I claim:

A new and distinct variety of white camellia japonica herein shown and described, characterized as to novelty by its vigorous growth, profuse blooming habits resulting in the production of large blossoms with petals curving inwardly at edges, luminous white in appearance, resistance to cold and disease, ease of propagation, and excellent keeping qualities.

KOSAKU SAWADA.